United States Patent [19]

Marshall et al.

[11] Patent Number: 4,876,243

[45] Date of Patent: Oct. 24, 1989

[54] VASOPRESSIN COMPOUNDS

[75] Inventors: Garland R. Marshall, Clayton, Mo.; Michael L. Moore, Media, Pa.

[73] Assignee: Smithkline Beckman Corporation, Philadelphia, Pa.

[21] Appl. No.: 89,886

[22] Filed: Aug. 27, 1987

Related U.S. Application Data

[63] Continuation-in-part of Ser. No. 832,805, Feb. 25, 1986.

[51] Int. Cl.$^4$ .................. A61K 37/34; C07K 7/16
[52] U.S. Cl. ........................................ 514/11; 530/315
[58] Field of Search ........................... 530/315; 514/11

[56] References Cited

U.S. PATENT DOCUMENTS

| | | | |
|---|---|---|---|
| 4,469,679 | 9/1984 | Huffman te al. | 514/11 |
| 4,481,193 | 11/1984 | Ali et al. | 514/11 |
| 4,481,194 | 11/1984 | Ali et al. | 514/11 |
| 4,491,577 | 1/1985 | Manning et al. | 514/11 |
| 4,543,349 | 9/1985 | Callahan et al. | 514/11 |

OTHER PUBLICATIONS

Turk, John et al., "Analogues of Angiotensin II with Restricted Conformational Freedom, Including a New Antagonist", *Molecular Pharmacology*, vol. 12, pp. 217–224 (1976).

Turk, John et al., "α-Methyl Substrates of Carboxy-γ-Peptidase A, Steric Probe of the Active Site" *Biochemistry*, vol. 14, No. 12, 1975.

Marshall, Garland, "Angiotensin II, Studies on the Biologically Active Conformation", Circulation Research II, vol. 30–31, pp. 143–150, 1972.

London, Robert E., "Testing for Cis'Proline with alpha-aminoisobutyric acid substitution", *Int. J. Peptide Protein Res.*, 19, pp. 334–342, 1982.

Manning, Maurice et al., "Carboxy Terminus of Vasopressin Required for Activity but Not Binding", *Nature*, vol. 12, pp. 652 & 653.

Strasser, Frans et al., "Molecular Mechanisms of Novel Antidiuretic Antagonists Analysis of the Effects on Vasopressin Binding and Adenylate Cyclase Activation in Animal and Human Kidney", *J. of Pharmacology and Experimental Therapeutics*, vol.223, No. 2, pp. 50–54 (1982).

Manning, Maurice et al., "Design of more Potent Antagonists of the Antidiuretic Responses of Arginine-Vasopressin", *J. Med. Chem.*, vol. 25, pp. 45–50 (1982).

*Primary Examiner*—Delbert R. Phillips
*Attorney, Agent, or Firm*—Charles M. Kinzig; Janice E. Williams; Alan D. Lourie

[57] ABSTRACT

Vasopressin-like peptide whose structures have been modified by an alpha-methyl amino acid at the 4 or 7 position are set forth. These compounds have potent vasopressin antagonist activities.

14 Claims, No Drawings

VASOPRESSIN COMPOUNDS

This application is a continuation-in-part of application Ser. No. 832,805 filed Feb. 25, 1986 which is pending.

This invention relates to vasopressin-like peptides whose structures are characterized by an α-methyl amino acid unit at either the 4 or 7 position. Such compounds have potent vasopressin antagonist activity.

BACKGROUND OF THE INVENTION

Many AVP antagonists have been reported in the literature. For example, des glycine d($CH_2$)$_5$VAVP compounds are described in U.S. Pat. No. 4,469,679 to have potent VSP antaqonist activity as are others with an intact side chain, M. Manning et al. Nature, 308 652 (1984) and U.S. Pat. No. 4,491,577. Deletion of the proline at position 7 of such structures also gave potent $V_2$-antagonism, U.S. Pat. Nos. 4,481,194 and 4,481,193.

α-Methylamino acid units have previously been introduced into biologically active peptides to study the conformational effect of introducing a sterically crowded amino acid for its normal counterpart. The biological activities of the resulting peptides have been indifferent. In such bradykinins, moderate or complete reduction in agonist activity was observed; R. E. London et al., Int. J. Peptide Res. 19 334–342 (1982). In angiotensin, the agonist activity was lost with α-Me units at some positions of the peptide structure, but activity is retained with substitution at other positions, e.g. positions 4 and 8 (Turk et al., Mol. Pharmacol., 12, 217 (1976), G.R. Marshall, Circulation Research, II of Vol. 30 31, 143 (1972). Therefore, the art in general shows that the activity of biologically active peptides with structures which include an α-methylamino acid unit is unpredictable.

In the description herein and in the claims, the nomenclature common in the art of peptide and, more specifically, vasopressin chemistry is used. When no configuration is noted, the amino acid unit is in the L, or naturally occurring, form. The thio members of the β-mercaptopropionic acid (1) and cysteine (6) units are added for clarity in certain structural formulas.

Exemplary of the peptide art designations used herein are the following: Pmp, β-mercapto-β,β-cyclopentamethylenepropionic acid; α-Me-AA, α-methyl aliphatic amino acid; Aib, α-aminoisobutyric acid or α-methylalanine; α-MeVal, α-methylvaline; α-MePro, α-methylproline; α-MeLys, α-methyllysine; α-MeArg, α-methylarginine; Tyr, tyrosine; Tyr(Alk), $C_{1-4}$-alkyl ether of tyrosine; Gly, glycine; Gly($NH_2$), glycinamide; Arg, arginine; MeArg, N-methyl-arginine (Nα-methyl); Cad, cadaverine; HArg, homoarginine; Phe, phenylalanine; 4'-AlkPhe, 4'-$C_{1-4}$-alkyl-phenylalanine; Val, valine; Chg, cyclohexylglycine; Gln, glutamic acid amide or glutamine; Cha, cyclohexylalanine; Lys, lysine; VSP, vasopressin; AVP, 8-arginine vasopressin; VAVP, 4-valine-8-arginine vasopressin; Asn, asparagine; Pro, proline; Cys, cysteine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HOBT, 1-hydroxybenzotriazole; ACM, acetamidomethyl.

DESCRIPTION OF THE INVENTION

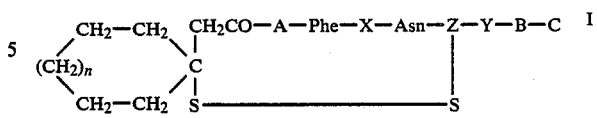

in which:
Z is a D or L isomer of Cys;
X is Val, Chg, Gln, Cha, Phe, Lys or α-MeAA;
Y is a D or L isomer of Pro, Arg, HArg or MeArg, a single bond, or α-MeAA, α-MePro, α-MeLys or α-MeArg; at last one of X and Y being a said α-Me amino acid group;
A is a D or L-isomer of Tyr, Tyr(Alk), Phe or 4'-Alk(Phe);
B is a D or L-isomer of Arg, MeArg, HArg; or, when C is Cad, a single bond.
C is Gly, Gly($NH_2$), Cad, OH or $NH_2$; and
n is 0 or 1, or a pharmaceutically acceptable salt or ester prodrug thereof.

One skilled in the VSP art will recognize that the units at X and Y are the distinguishing points of the chemical structures of the VSP antagonists of this invention.

A subgeneric group of the compounds of formula I are those in whose structures either X or Y is Aib.

Also included in this invention are various derivatives of the compounds of formula I such as addition salts, prodruqs in ester form and complexes. The addition salts may be either salt with pharmaceutically acceptable cations such as $NH^{\oplus}$, $Ca^{\oplus\oplus}$, $K^{\oplus}$ or $Na^{\oplus}$ at a terminal acid group, such as when C is Gly or OH is present, or with a pharmaceutically acceptable, acid addition salt at a basic center of the peptide such as in a Cad or Arg unit. The acetate salt forms are especially useful although hydrochloride, hydrobromide and salts with other strong acids are useful. In the isolation procedures outlined in the Examples, the peptide product is often isolated and purified as the acetate salt. The compounds also form inner salts or zwitter ions when a free terminal carboxy group is present.

Prodrugs are derivatives of the compounds of formula I which degrade to the parent compound in vivo. The ester prodrug forms are, for example, lower alkyl esters of the acids of formula I which have from 1–8 carbons in the alkyl radical or aralkyl esters which have 6–12 carbons in the aralkyl radical such as various benzyl esters. Such ester derivatives are prepared by methods known to the art. Other latentiated derivatives of the compounds of formula I will be obvious to those skilled in the art. "Complexes" include various solvates, such as hydrates or alcoholates, or those with supporting resins, such as a Merrifield resin.

The term "α-MeAA" is used to denote a unit of an α-methylaliphatic amino acid of the structure:

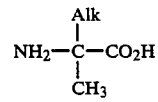

The term "Alk" is $C_{1-4}$-alkyl. These may be optionally branched. The α-MeAA unit may include optical isomers if an asymmetric carbon is present. Alk may be, for example, methyl, ethyl, isopropyl or isobutyl. Representative aliphatic amino acid units are alanine, valine, leucine, isoleucine. Therefore, the α-MeAA units comprise α-methylaliphatic amino acids of 4–7 carbons.

Alk, in the definition of A, is part of $C_{1-4}$ alkyl ether of tyrosine or a $C_{1-4}$ alkyl substituent in the phenyl ring of phenylalanine.

The compounds of formula I are prepared by cyclizing a linear peptide intermediate of this invention by means of the two mercapto groups located, respectively, in the cysteine unit at position 6 and in the Pmp unit at position 1. The cyclization reaction occurs in the presence of a mild oxidizing agent which, at high dilution, is capable of oxidizing intramolecularly the dimercaptan to a disulfide.

Oxidation of the following linear peptide;

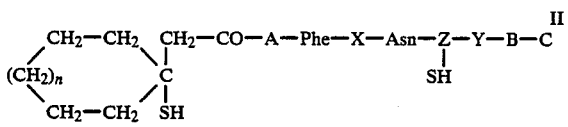

in which Z, X, Y, n, A, B and C are as defined for formula I, is carried out as described generally above. For example, an excess of an alkali metal ferricyanide, such as potassium or sodium ferricyanide, is used. The linear intermediate is dissolved in a suitable unreactive solvent, preferably in an aqueous solvent, at a neutral pH, about 7–7.5. The reaction is run at ambient temperature, or lower, until substantially complete. Lower alcohols, such as methanol, may be added. Preferably, the concentrations of the linear peptide dimercaptan and the oxidizing agent are low, say 0.01 molar concentration of oxidizing agent in several liters of aqueous solution to cyclize 1–6 grams of dimercaptan.

Other mild oxidation agents having an oxidation potential roughly equivalent to ferricyanide may also be used for the ring closure reaction. Oxygen, iodine, diiodoethane, hydrogen peroxide or cupric catalyzed oxidation are alternatives. Of course, one skilled in the art will recognize that certain cyclization methods are not appropriate if an interfering reaction site is present in the structure of the starting material of formula II. The linear mercaptan starting material may or may not have protecting groups common in the art present at the various amino acid units or at the mercapto positions. In the former case, the protecting groups are removed after cyclization. In the case of the ACM-SH protecting groups, removal of the protective group and cyclization may both be accomplished using iodine in aqueous methanol. Usually, however, the free linear peptide is cyclized.

The peptides of formula I are conveniently isolated by acidifying the aqueous oxidation mixture, such as using glacial acetic acid, and passing the reaction mixture over an ion exchange chromatographic column, for example, over a weakly acid, acrylic resin column with elution using buffered base, or by gel filtration over a bead formed gel prepared by cross linking dextran with epichlorohydrin. Often, the acetate salt is isolated by this method.

The important intermediates of formula II, in free or protected form are conveniently prepared using solid-phase methods of peptide synthesis as discussed in M. Manning et al., J. Med. Chem. 25 46 (1982). A commercial benzhydrylamine support resin (BHR) is used to prepare the amide end products of formula I, i.e. in which C is $NH_2$ or Gly($NH_2$), (the amides), and a chloromethyl support resin (CMR) is used to prepare the acid compounds of formula I, i.e. in which C is OH or Gly, (the acids). Solution or enzymatic synthetic methods can also be used.

The peptide chain of the linear peptides of formula II is built up, stepwise, proceeding from the C-terminal unit working toward the propionic acid unit at position 1. Each unit is properly protected as known in the peptide art and as described below. The sequence of step reactions is conveniently carried out in a Beckman 990-B peptide synthesizer without isolation of each intermediate peptide. The details of the overall synthetic procedure are in the working examples presented hereinafter.

The various amino acids, which are consecutively added to the resin supported chain are protected as known to the art. For example, the Boc protecting group is used for an amino group especially at the α-position of the amino acid; ethylcarbamoyl, adamantyl, t-butyl, acetamidomethyl, trityl or an optionally substituted benzyl, for the mercapto groups in the Pmp and Cys units; nitro; carbobenzoxy, methylene-2-sulfonyl or tosyl for a Arg, MeArg or HArg unit; and ethyloxycarbonyl or an optionally substituted carbobenzoxy(Z) for amino or hydroxyl groups. The protective groups should, most conveniently, be those which are easily removed, such as using acid treatment for the tert.-butyloxycarbonyl (Boc) group, sodium-liquid ammonia or modified catalytic hydrogenation for the benzyl or carbobenzoxy groups.

The deprotected peptide is obtained by treating the resin supported peptide with anhydrous hydrogen fluoride using a suitable carbonium ion scavenger, such as anisole, to give the linear peptide intermediate of formula II in good yield.

An alternative procedure for preparing the compounds of formula I is the attachment of one or more of the side chain units (A, B or C) to the acid form of the next lower peptide. For example, compounds of formula I in which C is cadaverine are prepared by the method described in U.S. Pat. No. 4,543,349. The condensation comprises the condensation of the polypeptide in the C-acid form with a side chain unit(s), whose acid or second basic center is protected, usually in the presence of DCC with HOBT or DMAP.

The compounds of this invention have potent $V_2$-$V_1$ vasopressin antagonist activity. Vasopressin is known to contribute to the anti diuretic mechanism of action within the kidney. When the action of the compounds of this invention antagonizes that of the natural anti-diuretic hormone (ADH), the body excretes water due to an increased permeability of the distal portions of the renal tubule. This mechanism of action is at the vasopressin receptors ($V_2$-receptors) located on the plasma membrane of certain renal epithelial cells. $V_2$-receptors affect the smooth muscle tissues of the blood vessels (and of the uterus). These are often referred to as vasopressor sites. The activity of these compounds is antagonistic in nature, not agonistic.

Any patient suffering from the syndrome of inappropriate antidiuretic hormone secretion (SIADH) or from an undesirable edematous condition is a target for compounds which have substantial $V_2$-antagonist activity. Examples of clinical conditions indicated for the present compounds include hypertension, hepatic cirrhosis, congestive heart failure or a component of any traumatic condition resulting from serious injury or disease.

The compounds of the present invention are, therefore, potent antagonists at $V_2/V_1$-receptor sites and thereby have potent water diuretic or antihypertensive activity in human or animal patients in need of such activity.

The compounds of this invention, therefore, are used to induce water diuresis antagonism, as noted above, in patients in need of such antagonist treatment by administration internally, particularly parenterally or by insufflation, to said patients. A non-toxic but effective quantity of the chosen compound is preferably combined with a pharmaceutical carrier. Dosage units contain a nontoxic, effective quantity of the active ingredient selected from the range 0.05-50 mcg/kg, preferably 1-15 mcg/kg, based on a 70 kg patient. The dosage units are administered from 1 to 5 times daily or by continuous intravenous drip.

The pharmaceutical compositions of this invention, which contain an active ingredient of formula I, comprise a dosage unit quantity as described above dissolved or suspended in a standard liquid carrier. Such a carrier is isotonic saline. The composition is often used in an ampoule or a multiple dose vial suitable for parenteral injection, such as for intravenous, subcutaneous or intramuscular administration. A composition for insufflation may be similar but is often administered in a metered dose applicator or inhaler. Pulverized powder compositions may be used along with oily preparations, gels, buffers for isotonic preparations, emulsions or aerosols.

Antagonistic activity at the $V_2$-vasopressin receptors is determined in a protocol which determines in vitro activity in pig tissue or in vivo diuretic activity in the hydropenic rat ($ED_{300}$ µg/kg). These procedures are described in the literature. F. Stassen et al., 1st International Conference on Diuretics, Miami, Fla., March (1984).

Antagonistic activity at the $V_1$-vasopressin receptors is determined in a protocol which measures the reversal of the vasopressin induced contraction of rat thoracic aorta tissue. This is expressed as $K_B$ (nM) in the table below. Such anti-pressor activity is confirmed in a similar in vitro protocol using the plasma membranes of rat liver. $V_2$-vasopressin antagonism is determined as receptor binding ability measured by inhibition of 3H-LVP binding ($K_B$ as nM), by inhibition of adenylate cyclase activation by vasopressin in the medullary tissue of hog kidneys (Ki as nM) or in vivo in the hydrogenic rat protocol ($ED_{300}$ µg/kg). These procedures are described in the literature: F. Stassen et al., J. Pharmacology and Experimental Therapeutics, 223 50 (1982).

TABLE 1

| Compound | Representative Antagonist Activities | | | |
|---|---|---|---|---|
| | Pig $V_2$ | | Rat $V_1$ | Rat $V_2$ |
| | Ki (nM) | $K_B$ (nM) | $K_B$ (nM) | $ED_{300}$ (µg/kg) |
| A | 18 | 9.2 | — | 22.7 |
| B | 140 | 580 | — | 39.9 |
| C | 31 | 11 | — | 18 |
| D | 490 | 170 | 18 | 61 |
| E | 16 | 15 | — | 72.8 |
| F | 88 | 35 | 12 | 98 |
| G | 12 | 6.7 | 1.4 | 11 |

The structures of the compounds of Table 1 are as follows:

A. [1-(β,β-cyclopentamethylene-β-mercaptopropionic acid)-2-(O-ethyl-D-tyrosine)-4-valine-7-α-aminoisobutyric acid-8-arginine]vasopressin.

B. [1-(β,β-cyclopentamethylene-β-mercaptopropionic acid)-2-(O-ethyl-D-tyrosine)-4-α-aminoisobutyric acid-8-arginine-9-desglycine]vasopressin.

C. [1-(β,β-cyclopentamethylene-β-mercaptopropionic acid)-2-(O-ethyl-D-tyrosine)-4-α-methylvaline-8-arginine]vasopressin.

D. [1-(β,β-cyclopentamethylene-β-mercaptopropionic acid)-2-(O-methyl L-tyrosine)-4-α-methylvaline-8-arginine]vasopressin.

E. [1-(β,β-cyclopentamethylene-β-mercaptopropionic acid)-2-(O-ethyl-D-tyrosine)-4-valine-7-α-aminoisobutyric acid-8-arginine-9-desglycine]vasopressin.

F. [1-(β,β-cyclopentamethylene-β-mercaptopropionic acid)-2-(O-methyl-L-tyrosine)-4-valine-8-arginine]vasopressin.

G. [1-(β,β-cyclopentamethylene-β-mercaptopropionic acid)-2-(O-ethyl-D-tyrosine)-4-valine-8-arginine]vasopressin.

The data in Table 1 demonstrate the antagonist activity of representative compounds of this invention whose structures have an unnatural α-methyl amino acid unit. Compounds F and G are representative compounds of the prior art.

The following examples are designed solely to teach the operation of this invention. All temperatures are degrees Centigrade. Nomenclature is standard in the peptide art.

EXAMPLE 1

Preparation of Protected α-Methylamino Acids

A. 5.0 G of Aib (48 mmol) was dissolved in 15 ml of water containing 2.0 g of sodium hydroxide (1 eq.) and 25 ml of t-butanol. To this was added 11.5 q of t-butyldicarbonate (1.1 eq.) dropwise over 30 minutes. The reaction mixture was allowed to stir overnight. The turbid reaction mixture was diluted with 25 ml of water and extracted with hexane (3×50 ml). The aqueous layer was then acidified to pH 2-3 with solid sodium bisulfate (7.1 g) and extracted with ethyl acetate (3×50 ml). The ethyl acetate extracts were combined, dried over anhydrous sodium sulfate and evaporated to yield 4.9 g of Boc-Aib (51%), m.p. 117°-118° (after drying in vacuum); elemental analysis: C, 53.19; H, 8.43; N, 6,89; (calculated); C, 53.30; H, 8.26; N, 7.10 (found).

B. 1 G (7.63 mmol) of L-α-MeVal was suspended in 30 ml of dimethylformamide and stirred with 2.14 g of t-butyl-dicarbonate (9.80 mmol) and tetramethylguanidine (TMG) (1.13 g) for 20 hours. Another portion of carbonate and TMG was added and the mixture stirred for one more day.

The solvents were removed by evaporation and the residue taken up in 150 ml of water, washed with ether and, then, acidified with dilute sulfuric acid to pH 2.5. The turbid material was extracted into ethyl acetate, washed twice with water, dried over sodium sulfate and evaporated to dryness to give 0.64 g of light colored oil which gradually turned into solid Boc-α-MeVal.

EXAMPLE 2

Solid Phase Synthesis of Supported Linear Peptide-BHA Starting Material

For the solid phase synthesis of the titled resin-supported peptides, a 7, 8 or 9-position unit resin material, for example, Boc Arg(Tos)BHA resin or Boc-Gly-BHA resin (1.00 mmol/g of resin), is used as a starting material. It is prepared by reacting Boc-Amino Acid- (Tos if necessary), 3 mmol, with the benzhydrylamine resin, 1.0 mmol, in dimethylformamide for two hours. The benzhydrylamine resin as a free base is swollen in methylene chloride overnight. It is washed once with 7% diisopropylethylamine (DIEA) in methylene chloride, then 6×1 min. with methylene chloride, and finally 2×1 min. with predried dimethylformamide. The loading of Boc-amino acid on the resin is carried out twice on the shaker using 1-hydroxybenzotriazole (HOBT, 3 mmol), and dicyclohexylcarbodiimide (DCC, 3 mmol) or other coupling agents. A quantitative ninhydrin test and amino acid analysis are performed routinely after loading to determine the percentage loading on the resin.

The appropriately protected amino acids are coupled sequentially on the Boc-amino acid-resin using the Beckman peptide synthesizer 990-B or a manual shaker. The program used for each coupling, except Boc-Asn and Pmp(4-MeBzl), is as follows:

(1) Wash with methylene chloride (3 times, 1 min).
(2) Prewash with 50% trifluoroacetic acid in methylene chloride (1 time, 1 min).
(3) Deprotect with 50% trifluoroacetic acid in methylene chloride (20 min).
(4) Wash with methylene chloride (3 times, 1 min).
(5) Prewash with 7% DIEA in methylene chloride (1 time, 1 min).
(6) Neutralize with 7% DIEA in methylene chloride (1 time, 10 min).
(7) Wash with methylene chloride (3 times, 1 min).
(8) Protect amino acid (3 mmol) in methylene chloride, followed by addition of DCC, 3 mmol, 10 ml of 0.3M in methylene chloride, and coupling for two hours.
(9) Wash with methylene chloride (3 times, 1 min).
(10) Wash with ethanol/methylene chloride (1:1 (3 times, 1 min).
(11) Wash with methylene chloride (3 times, 1 min).

In case of coupling of Asn moiety, 1-hydroxybenzotriazole (HOBT, 3 mmol) is used, 10 ml of 0.6M in dimethylformamide. Dry dimethylformamide may also be used as solvent when Pmp(4-MeBzl) is coupled onto the peptide resin, using 4-dimethylaminopyridine (DAP, 3 mmol). Completion of each coupling reaction is monitored by the ninhydrin test. The p-methylbenzyl group is often used to protect the thiol groups of Cys and the Pmp moieties.

The benzhydrylamine resin is analyzed by nitrogen analysis to fall usually within 0.72–1.03 mmol per 1 gram. Each protected amino acid unit is purchased from commercial sources of synthesized by known procedures as noted above. Successful coupling incorporates 0.4 to 0.732 mmole per gram of the first amino acid.

EXAMPLE 3

[Pmp$^1$-D-Tyr(Et)$^2$-Aib$^4$-Arg$^8$desGly$^9$]VSP

The standard solid phase method on BHA resin as described in Example 2 was employed but using diisopropylcarbodiimide/HOBt as the coupling agent on a 1 mmole scale. The peptide was cleaved from the resin with anhydrous hydrogen fluoride and cyclized in dilute aqueous solution at pH 7.2 with potassium ferricyanide. The oxidized peptide was passed over an HP-20 polystyrene column which was washed with water and, then, eluted with 50% acetonitrile (aq) containing 1% trifluoroacetic acid. The eluate was evaporated to dryness and the residue lyophilized from 1% acetic acid to give 303 mg of the crude titled peptide.

The crude peptide was purified by countercurrent distribution in the system of n BuOH/HOAc/H$_2$O (4:1:5), 240 transfers, yielding 157 mg of partially purified peptide after evaporation of the solvent and lyophilization of the residue. 100 mg of this partially purified peptide was, then, passed over a P-2 gel filtration column in 1% acetic acid to give 73 mg of purified peptide: homogeneous by tlc and hplc; FABMS m/z 1065 (M+H$^+$); amino acid analysis, Asp 1.02, Pro 0.92, Cys 0.72, Tyr 0.95, Phe 0.97, Arg 1.00; peptide content 73%.

EXAMPLE 4

[Pmp$^1$-D-Tyr(Et)$^2$-Val$^4$-Aib$^7$-Arg$^8$]VSP

Peptide synthesis was by the standard solid phase method on BHA resin using DCC/HOBt as the coupling agent on a 1 mmole scale. After cleavage of the peptide from the resin with anhydrous hydrogen fluoride, the peptide was oxidized in a dilute aqueous solution at pH 7.2 with potassium ferricyanide. The oxidized peptide was passed over an HP-20 polystyrene column which was, then, washed with water and eluted with 50% acetonitrile (aq) containing 1% trifluoroacetic acid. The eluate was evaporated to dryness and the residue was lyophilized from water.

The crude peptide was purified by countercurrent distribution in the system n BuOH/HOAc/H$_2$O (4:1:5), 240 transfers, which yielded 423 mg of partially purified peptide. 100 mg of the partially purified peptide was passed over a G-15 gel filtration column in 1% acetic acid, yielding 78 mg of the titled purified peptide: homogeneous by tlc and hplc; FABMS m/z 1124 (M+H$^+$); amino acid analysis, Asp 0.97, Gly 1.00, Aib 0.89, Cys 0.63, Val 0.85, Tyr 0.78, Phe 0.85, Arg, 0.86; peptide content 60%.

EXAMPLE 5

[Pmp$^1$-Tyr(Me)$^2$-$\alpha$-MeVal$^4$-Arg$^8$]VSP 2.56 G (0.39 mmol/g) of Boc-Gly-OCH$_2$C$_6$H$_4$-resin was placed in a 990B synthesizer and reacted with 3 mmols of each Boc-protected amino acid unit using DCC and HOBt. DMAP was added for coupling the protected $\alpha$-MeVal and Pmp units. Bzl was used to protect S in the Pmp and Cys units, Tos for Arg nitrogen. The protected resin peptide was ammonolyzed in 200 ml methanol saturated with ammonia and 50 ml dimethylformamide at room temperature for 48 hours with stirring. After filtering off the resin, the filtrate was evaporated to dryness and triturated with hexane/ethyl acetate to give the crude, protected peptide as a powder.

This crude peptide was dissolved in 250 ml liquid ammonia and treated with a sodium/liquid ammonia solution to give the crude, deprotected linear peptide after evaporation of the ammonia. This was then dissolved in water (4 l) and, after adjusting to pH 7.2, oxidized with 0.01 M potassium ferricyanide. The solution was lowered to pH 4.5 with glacial acetic acid and the peptide was passed over a BioRex 70 cation exchange column (H+ form). After washing with water, the column was eluted with 200 ml pyridine/water/acetic acid (30:64:6). The crude oxidized peptide thus obtained was purified as described previously to give 40 mg of the product.

EXAMPLE 6

[Pmp$^1$-D-Tyr(Et)$^2$-Aib$^4$-desPro$^7$-Arg$^8$-Arg$^9$]VSP

The protected peptide intermediate resin, Pmp(4-MeBzl)-D-Tyr(Et)-Phe-Aib Asn-Cys(4-MeBzl)-Arg(Tos)-Arg(Tos)-BHA is synthesized by solid phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed through a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 7

[Pmp$^1$-D-Tyr(Et)$^2$-Val$^4$-Aib$^7$-Arg$^8$-Gly$^9$]VSP

The protected peptide intermediate resin, Pmp(4-MeBzl)-D-Tyr(Et)-Phe-Val-Asn-Cys(4-MeBzl)-Aib-Arg(Tos)-Gly-BHA is synthesized by solid phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed throuqh a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 8

[Pmp$^1$-D-Tyr(Et)$^2$-Aib$^4$-Pro$^7$-Arg$^8$]VSP

The protected peptide intermediate resin, Pmp(4-MeBzl)-D-Tyr(Et)-Phe-Aib-Asn-Cys(4-MeBzl)-Pro-Arg(Tos)-BHA is synthesized by solid phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed through a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 9

[Pmp$^1$-D-Tyr(Et)$^2$-α-MeVal$^4$-Pro$^7$-Arg$^8$-Gly$^9$]VSP

The protected peptide intermediate resin, Pmp(4-MeBzl)-D-Tyr(Et)-Phe-α-MeVal-Asn-Cys(4-MeBzl)-Pro-Arg(Tos)-Gly-BHA is synthesized by solid phase methods on benzhydrylamine resin (BHA). On a shaker, 1.0 mmol of the BHA resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed through a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 10

[Pmp$^1$-Tyr(Me)$_2$-α-MeVal$^4$-Pro$^7$Arg$^8$-Gly$^9$]VSP

The protected peptide intermediate resin, Pmp(4-MeBzl)-Tyr(Me)-Phe-α-MeVal-Asn-Cys(4-MeBzl)-Pro-Arg(Tos)-Gly-BHA is synthesized by solid phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed through a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 11

[Pmp$^1$-D-Tyr(Et)$^2$-Val$^4$-Aib$^7$-Arg$^8$]VSP

The protected peptide intermediate resin, Pmp(4-MeBzl)-D-Tyr(Et)-Phe-Val-Asn-Cys(4-MeBzl)-Aib-Arg(Tos)-BHA is synthesized by solid phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Pmp(4-MeBzl) is coupled using DCC/DMAP. The peptide is cleaved from the resin with deprotection of the side chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persisted for 15 minutes. The pH of the solution is adjusted to 4.5 using glacial acetic acid. It is passed through a weakly acid, acrylic resin (Bio-Rex 70) column. The column is eluted with pyridine acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 12

[Pmp$^1$-D-Tyr(Et)$^2$-α-MeVal$^4$-desPro$^7$-Arg$^8$-Arg$^9$]VSP

The protected peptide intermediate used, Pmp(4-MeBzl)-D-Tyr(ET)-Phe-α-MeVal-Asn-Cys(4-MeBzl)-Arg-(Tos)-Arg (Tos)-OCH$_2$C$_6$H$_4$-Resin is synthesized on 1.0 mmol of Boc-Arg(Tos)-O-Bzl-Resin (purchased from Peninsula Laboratories). The HF cleavage and oxidation with 0.01 M ferricyanide are performed as described above. The dilute solution is partially purified through a reversed phase C-18 column. The titled peptide is eluted with 50% aqueous acetonitrile containing 0.1% trifluoroacetic acid. Further purification by preparative HPLC as described above.

EXAMPLE 13

[Pmp$^1$-D-Tyr(Et)-Aib$^4$-Cad$^8$-desGly(NH$_2$)$^9$]VSP

To a solution of the Pmp$^1$-proline$^7$ heptapeptide, prepared as described in U.S. Pat. No. 4,543,349 and in Example 2, (0.0331 mmol) and mono-Boc-1,5-diaminopentane (20.2 mg, 0.0996 mmol) in dimethylformamide (400 l), dicyclohexylcarbodiimide (10.3 mg, 0.05 mmol) and 1-hydroxybenzotriazole hydrate (13.4 mg, 0.1 mmol) are added. The reaction mixture is stirred at room temperature for 19 hours. The dimethylformamide is, then, removed under vacuum. The residue is treated with trifluoroacetic acid at 0° for 2 hours. After this time, the trifluoroacetic acid is removed under vacuum and the residue in 1% acetic acid is passed over a BioRex 70 (H$^+$) ion exchange column. The basic products are washed off the ion exchange column with pyridine buffer (H$_2$O/pyridine/HOAc, 66:30:4) and evaporated. Final purification by prep HPLC (5 Ultrasphere ODS) gives the title compound.

EXAMPLE 14

[Pmp$^1$,D-Tyr(Et)$^2$,Val$^4$,D-Cys$^6$,Aib,$^7$,Arg$^8$,desGly$^9$]VSP

The protected peptide intermediate resin Pmp(4-MeBzl)-D-Tyr(Et)-Phe-Val-Asn-D-Cys(4-MeBzl)-Aib-Arg(Tos)-BHA is prepared by the standard solid phase method described in Example 2. The peptide is cleaved from the resin with anhydrous hydrogen fluoride and is then cyclized in dilute aqueous solution at pH 7.2 with potassium ferricyanide. The oxidized peptide is passed over an HP-20 polystyrene column, which is then washed with water and eluted with 50% aqueous acetonitrile containing 1% trifluoracetic acid. The eluate is evaporated to dryness and the residue lyophilized from 1% acetic acid to give the crude peptide.

The crude peptide is purified by countercurrent distribution in the system of n-BuOH/HOAc/H$_2$O (4:1:5) followed by gel filtration on Sephadex G-15 using 1% acetic acid as eluant to yield the purified peptide.

EXAMPLE 15

[Pmp$^1$,D-Tyr(Et)$^2$,Val$^4$,α-Mepro$^7$, Arg$^8$,desGly$^9$]VSP

The protected peptide intermediate resin Pmp(4-MeBzl)-D-Tyr(Et)-Phe-Val-Asn-Cys(4-MeBzl)-α-MePro-Arg(Tos)-BHA is prepared by the standard solid phase method described in Example 2. The peptide is cleaved from the resin with anhydrous hydrogen fluoride and is then cyclized in dilute aqueous solution at pH 7.2 with potassium ferricyanide. The oxidized peptide is passed over an HP-20 polystyrene column, which is then washed with water and eluted with 50% aqueous acetonitrile containing 1% trifluoroacetic acid. The eluate is evaporated to dryness and the residue lyophilized from 1% acetic acid to give the crude peptide.

The crude peptide is purified by countercurrent distribution in the system of n-BuOH/HOAc/H$_2$O (4:1:5) followed by gel filtration on Sephadex G-15 using 1% acetic acid as eluant to yield the purified peptide.

EXAMPLE 16

Using the methods of synthesis described in detail above, the following specific compounds are produced.

a. [1-(β,β-cyclotetramethylene-β-mercaptopropionic acid)-2-(4'-ethylphenylalanine)-4-valine-7-α-aminoisobutyric acid-8-arginine]vasopressin;

b. [1-(β,β-cyclopentamethylene-β-mercaptopropionic acid)-2-(O-ethyl-D-tyrosine)-4-α-methylisoleucine-7-desproline-8-homoarginine-9-desglycine]vasopressin;

c. [1-(β,β-cyclopentamethylene-β-mercaptopropionic acid)-2-(O-ethyl-D-tyrosine)-4-valine-7-α-aminoisobutyric acid-8-N-methylarginine]vasopressin;

d. [1-(β,β-cyclopentamethylene-β-mercaptopropionic acid)-2-D-tyrosine-4-valine-7-α-methylleucine-8-arginine]vasopressin.
e. [1-(β,β-cyclopentamethylene-β-mercaptopropionic acid)-2-(O-ethyl-D-tyrosine)-4-α-aminoisobutyric acid-8-D-arginine]vasopressin;
f. [1-(β,β-cyclopentamethylene-β-mercaptopropionic acid)-2-(O-ethyl-D-tyrosine)-4-valine-7-α-aminoisobutyric acid-8-arginine-9-desglycinamide]vasopressin;
g. [1-(β,β-cyclopentamethylene-β-mercaptopropionic acid)-2-(O-ethyl-D-tyrosine)-4-valine-7-α-aminoisobutyric acid-8-arginine-9-desglycine]vasopressin.

EXAMPLE 17

Parenteral Dosage Unit Compositions:

A preparation which contains 0.01 mg of the peptide of Example 4 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin V₂-antagonist treatment as necessary, from 1-5 times daily by injection, or in an equivalent continuous i.v. drip injection.

Nasal Dosage Unit Compositions:

2.5 mg of a finely ground peptide of this invention, such as the product of Example 4, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a subject in need of aquaretic therapy from 1-6 times a day.

What is claimed is:

1. A chemical compound having the formula:

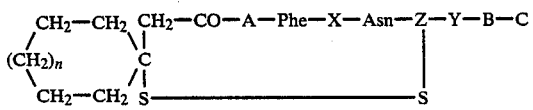

in which:

Z is a D or L-isomer of Cys;
X is Val, Chg, Gln, Cha, Phe, Lys or α-MeAA;
Y is a D or L-isomer of Pro, Arg, HArg or MeArg, a single bond or α-MeAA, α-MePro, α-MeLys or α-MeArg; at least one of X and Y being a said α-Me amino acid group;
A is a D or L-isomer of Tyr, Tyr(Alk), Phe or 4'-AlkPhe;
B is a D or L-isomer of Arg MeArg or HArg or, when C is Cad, a single bond;
C is Gly, Gly(NH₂), Cad, OH or NH₂; and
n is 0 or 1, or a pharmaceutically acceptable salt or ester prodrug thereof.

2. The compound of claim 1 in which X is α-MeAA and C is NH₂.

3. The compound of claim 1 in which Y is α-MeAA and C is Gly(NH₂).

4. The compound of claim 1 in which Y and B are both Arg.

5. The compound of claim 2 in which α-MeAA is Aib.

6. The compound of claim 3 in which α-MeAA is Aib.

7. The compound of claim 1 which is [1-(β,β-cyclopentamethylene-β-mercaptopropionic acid)-2-(O-ethyl-D-tyrosine)-4-valine-7-α-aminoisobutyric acid-8-arginine]-vasopressin or a pharmaceutically acceptable salt thereof.

8. The compound of claim 1 which is [1-(β, β-cyclopentamethylene-β-mercaptopropionic acid)-2-(O-ethyl-D-tyrosine)-4-α-aminoisobutyric acid-β-arginine-9-desglycine]vasopressin or a pharmaceutically acceptable salt thereof.

9. The compound of claim 1 which is [1-(β,β-cyclopentamethylene-β-mercaptopropionic acid)-2-(O-ethyl-D-tyrosine)-4-α-methylvaline-8-arginine]-vasopressin or a pharmaceutically acceptable salt thereof.

10. A pharmaceutical composition having vasopressin antagonist activity comprising a pharmaceutical carrier and, dispersed therein, an effective therefor but nontoxic quantity of a compound of claim 1.

11. A pharmaceutical composition having vasopressin antagonist activity comprising a pharmaceutical carrier and, dispersed therein, an effective therefor but nontoxic quantity of the compound of claim 7.

12. A pharmaceutical composition having vasopressin antagonist activity comprising a pharmaceutical carrier and, dispersed therein, an effective therefor but nontoxic quantity of the compound of claim 8.

13. The method of producing vasopressin antagonist activity in a patient in need thereof which comprises administering parenterally or intranasally to said patient an effective therefor, nontoxic quantity of a compound of claim 1.

14. The method of producing vasopressin antagonist activity in a patient in need thereof which comprises administering parenterally or intranasally to said patient an effective therefor, nontoxic quantity of the compound of claim 7.

* * * * *